(12) United States Patent
Miller

(10) Patent No.: US 12,390,417 B2
(45) Date of Patent: Aug. 19, 2025

(54) PRAZIQUANTEL FORMULATIONS

(71) Applicant: Villya LLC, Melbourne, FL (US)

(72) Inventor: William Miller, Melbourne, FL (US)

(73) Assignee: Villya LLC, Melbourne, FL (US)

(*) Notice: Subject to any disclaimer, the term of this patent is extended or adjusted under 35 U.S.C. 154(b) by 0 days.

(21) Appl. No.: 17/583,738

(22) Filed: Jan. 25, 2022

(65) Prior Publication Data

US 2022/0142920 A1 May 12, 2022

Related U.S. Application Data

(63) Continuation of application No. 16/991,397, filed on Aug. 12, 2020, now abandoned.

(51) Int. Cl.
| | |
|---|---|
| *A61K 9/08* | (2006.01) |
| *A61K 9/00* | (2006.01) |
| *A61K 31/4985* | (2006.01) |
| *A61K 47/10* | (2017.01) |
| *A61K 47/26* | (2006.01) |

(52) U.S. Cl.
CPC ............ *A61K 9/08* (2013.01); *A61K 9/0095* (2013.01); *A61K 31/4985* (2013.01); *A61K 47/10* (2013.01); *A61K 47/26* (2013.01)

(58) Field of Classification Search
CPC ...................................................... A61K 9/08
See application file for complete search history.

(56) References Cited

U.S. PATENT DOCUMENTS

| | | |
|---|---|---|
| 6,159,932 A | 12/2000 | Mencke et al. |
| 6,224,573 B1 | 5/2001 | Yeager et al. |
| 6,416,779 B1 | 7/2002 | D'Augustine et al. |
| 7,258,873 B2 | 8/2007 | Truong-Le et al. |
| 8,034,765 B2 | 10/2011 | De et al. |
| 8,461,115 B2 | 6/2013 | Uttenthal |
| 8,551,507 B2 | 10/2013 | Liu |
| 8,840,869 B2 | 9/2014 | Friedman et al. |
| 9,333,329 B2 | 5/2016 | Ziv |
| 10,201,576 B2 | 2/2019 | Rishi |
| 10,350,042 B2 | 7/2019 | Schuman et al. |
| 10,391,134 B2 | 8/2019 | Meuwly et al. |
| 10,555,900 B2 | 2/2020 | Podolski et al. |
| 10,662,259 B2 | 5/2020 | Russo et al. |
| 10,857,151 B1 | 12/2020 | Miller |
| 11,364,203 B2 | 6/2022 | Vodak et al. |
| 2002/0081292 A1 | 6/2002 | Jancys |
| 2004/0198676 A1 | 10/2004 | Soll et al. |
| 2006/0147388 A1 | 7/2006 | Merkus et al. |
| 2006/0292225 A1 | 12/2006 | Felix et al. |
| 2009/0018175 A1 | 1/2009 | Kanari et al. |
| 2009/0036458 A1 | 2/2009 | Fattohi et al. |
| 2011/0033525 A1 | 2/2011 | Liu |
| 2012/0329738 A1 | 12/2012 | Liu |
| 2014/0094418 A1 | 4/2014 | Isele |
| 2015/0359898 A1 | 12/2015 | Purandare et al. |
| 2016/0083385 A1 | 3/2016 | Liu et al. |
| 2016/0272636 A1 | 9/2016 | Qian et al. |
| 2019/0160332 A1 | 5/2019 | Beer et al. |
| 2019/0223481 A1 | 7/2019 | Gaspard et al. |
| 2019/0290474 A1 | 9/2019 | Simpson et al. |
| 2021/0068425 A1 | 3/2021 | Ross et al. |
| 2021/0260062 A1 | 8/2021 | Miller |

FOREIGN PATENT DOCUMENTS

| | | | |
|---|---|---|---|
| CN | 105816421 B | | 1/2019 |
| DE | 3619030 A1 | | 12/1987 |
| EP | 3868381 A1 | | 8/2021 |
| RU | 2681214 C1 | | 3/2019 |
| WO | WO-99/041233 A1 | | 8/1999 |
| WO | 0078149 A1 | | 12/2000 |
| WO | WO-01/049268 A1 | | 7/2001 |
| WO | WO-2007/011349 A1 | | 1/2007 |
| WO | 2008/077130 A2 | | 6/2008 |
| WO | 2009/109966 A1 | | 9/2009 |
| WO | 2011047227 A2 | | 4/2011 |
| WO | 2011/098579 A1 | | 8/2011 |
| WO | WO2015071668 | * | 5/2015 |
| WO | 2016090240 A1 | | 6/2016 |
| WO | WO2016143939 | * | 9/2016 |
| WO | 2020061584 A1 | | 3/2020 |

OTHER PUBLICATIONS

English Translation of WO 2016/143939 publication of PCT/KR2015/003643 downloaded from https://patentscope.wipo.int/search/en/detail.jsf?docId=WO2016143939.

Patel et al. "Formulation and Development Strategies for Drugs Insoluble in Gastric Fluid" International Research Journal of Pharmacy, 2012, 3 (1), pp. 106-113.

Jatwani et al. "An Overview on Solubility Enhancement Techniques for Poorly Soluble Drugs and Solid Dispersion as an Eminent Strategic Approach" International Journal of Pharmaceutical Sciences and Research, 2012, vol. 3(4), pp. 942-956.

Nov. 17, 2021—(WO) Notification of Transmittal of the International Search Report and Written Opinion—Appl No. PCT/US2021/044665.

Liu et al. "Dissolution and oral bioavailability enhacement of praziquantel by solid dispersions" Drug Delivery and Translational Research, vol. 8 (Feb. 15, 2018), pp. 580-590.

Pakharukova et al. "The first comprehensive study of praziquantel effects in vivo and in vitro on European liver luke *Opisthorchis felineus* (*Trematoda*)" International Journal of Antimicrobial Agents, vol. 46, (Jul. 2015), pp. 94-100.

Jeon et al. "Differential diagnosis of Taenia asiatica using multiplex PCR" Experimental Parasitology, vol. 121 (Nov. 5, 2008), pp. 151-156.

May 24, 2024—(WO) International Search Report and Written Opinion—App PCT/US2024/012426.

(Continued)

*Primary Examiner* — Sarah Alawadi

(74) *Attorney, Agent, or Firm* — Banner & Witcoff, Ltd.

(57) ABSTRACT

Praziquantel may be formulated to enhance its pharmacokinetic, toxicity, and palatability properties. It can be stored and/or dispensed as a liquid, powder, or tablet. Reduction in the most common side effects improves patient compliance and satisfaction. Altered taste profile improves patient compliance and satisfaction. Once formulated it can be used to treat a variety of blood flukes and worms in human and veterinary subjects.

22 Claims, No Drawings

(56) References Cited

OTHER PUBLICATIONS

Zhijun Liu: "Cytotoxic and antiangiogenic paclitaxel solubilized and permeation-enhanced by natural product nanoparticles", Anti-Cancer Drugs, [Online] vol. 26, No. 2, Feb. 1, 2015 (Feb. 1, 2015), pp. 167-179, XP093159605.
Ratna M Kharisma: "Dissolution Rate Repairing of Simvastatin as a New Approach in Cocrystallization", Der Pharmacia Lettre, [Online] vol. 9, No. 6, Jan. 1, 2017 (Jan. 1, 2017), pp. 18-27, XP093159779.
"Female Genital Schistosomiasis, A Pocket Atlas for clinical Health-Care Professionals," WHO Library Cataloguing-in-Publication, 2015Data.
Treatment of FGS with Praziquantel at https://clinicaltrials.gov/ct2/show/ NCT04115072 at https://clinicaltrials.gov/ct2/show/NCT04115072 (retrieved from the internet Jul. 8, 2020) (Year: 2019).
Alexander et al. "Why consider vaginal drug administration?" Fertility and Sterility; vol. 82; No. 1; Jul. 2004; pp. 1-12.
Zanolla et al. "A new soluble and bioactive polymorph of praziquantel" European Journal of Pharmaceutics and Biopharmaceutics; 127 (2018) 19-28.
Bribeche et al. "Topical praziquantel as a new treatment for perioral dermatitis: results of a randomized vehicle-controlled pilot study" Clinical and Experimental Dermatology; (2014) 39, pp. 448-453.
Goodman & Gilman's The Pharmacological Basis of Therapeutics (Tenth Edition (2001), McGraw Hill, Chapter 1, pp. 3-29 (Year: 2001).
Hotez et al. "Female genital schistosomiasis and HIV/AIDS: Reversing the neglect of girls and women" PLOS Neglected Tropical Diseases, (2019).
Abla et al. "Evaluation of the pharmacokinetic-pharmacodynamic relationship of praziquantel in the Schistosoma mansoni mouse model" PLOS Neglected Tropical Diseases, Sep. 21, 2017.
El-Feky et al. "Praziquantel in a Clay Nanoformulation Shows More Bioavailability and Higher Efficacy against Murine Schistosoma mansoni Infection" Antimicrobial Agents and Chemotherapy, Jun. 2015, vol. 59, No. 6, pp. 3501-3508.
Kjetland et al. "Genital schistosomiasis in women: a clinical 12-month in vivo study following treatment with praziquantel" Transactions of the Royal Society of Tropical Medicine and Hygiene, vol. 100, No. 8, Aug. 1, 2006, pp. 740-752.
Jul. 27, 2021—(EP) Extended European Search Report and Search Opinion—Appln. No. 21158508.8.
Rowe et al. "Propylene Glycol" Handbook of Pharmaceutical Excipients; 6th ed.; Pharmaceutical Press; Published 2009; pp. 592-594.
Pearson; Schistosomiasis (Bilharziasis); Merck Manuals Professional Edition; Revised May 2018.
Zou et al. "Application of Pharmacokinetic-Pharmacodynamic Modeling in Drug Delivery: Development and Challenges" Frontiers in Pharmacology; Published Jul. 3, 2020; vol. 11; No. 997.
Block "Chapter 29: Medicated Topicals" Remington Essentials of Pharmaceutics; Edited by Linda Felton; Pharmaceutical Press; 1st edition; pp. 565-579; Published 2013.
Shelley Fox; "Remington Education: Pharmaceutics" Pharmaceutical Press; 1st edition; p. 1-17; 2014.
Extended European Search Report issued Jul. 27, 2021 in European Patent Application No. 21158508.8.
Communication under Rule 71(3) EPC—Intention to Grant issued Feb. 27, 2023 in European Patent Application No. 21158508.8.
Brotto, V. et al. Clinical Dosage Calculations, 3rd edition. Cengage Learning Australia, 2019: 98-117. (Year: 2019).
Hloch, S. et al. Advances in Manufacturing Engineering and Materials. Springer International Publishing, 2018: 66-67. (Year: 2018).
Srikrishna, S. et al. "The vagina as a route for drug delivery: a review." International urogynecology journal, 2013. vol. 24,4: 537-43. (Year: 2013).
Fulcher, E. M. et al. Pharmacology, 3rd edition, 2011. Elsevier Health Science: 39-52 (Year: 2011).
Wen, H. et al. Oral Controlled Release Formulation Design and Drug Delivery: Theory to Practice. Wiley, 2011 :121. (Year: 2011).
Non-Final Office Action issued Oct. 5, 2023 in U.S. Appl. No. 17/109,531.
Final Office Action issued Jan. 10, 2024 in U.S. Appl. No. 17/109,531.
U.S. Appl. No. 17/109,531, filed Dec. 2, 2020.
Jul. 5, 2024 (EP) Extended European Search Report—App 21856462.3.
Gaggero et al., "Cogrinding with surfactants as a new approach to enhance in vitro dissolution of praziquantel," *Journal of Pharmaceutical and Biomedical Analysis*, vol. 189, 12 pages, 2020.
Holvoet et al., "Preparation and evaluation of paclitaxel-containing liposomes," *Die Pharmazie—An International Journal of Pharmaceutical Sciences*, vol. 62, pp. 126-132, 2007.
Kannan et al., "Effect of sucrose as a lyoprotectant on the integrity of paclitaxel-loaded liposomes during lyophilization," *Journal of Liposome Research*, Early Online, pp. 1-9, 2014.
Liu et al., "Cytotoxic and antiangiogenic paclitaxel solubilized and permeation-enhanced by natural product nanoparticles," *Anti-Cancer Drugs*, vol. 26, No. 2, pp. 167-179, 2015.
Yang et al., "Liposome Formulation of Paclitaxel with Enhanced Solubility and Stability," *Drug Delivery*, vol. 14, pp. 301-308, 2007.
Zhang et al., "A Novel Solubility-Enhanced Rubusoside-Based Micelles for Increased Cancer Therapy," *Nanoscale Research Letters*, vol. 12, No. 274, 10 pages, 2017.

\* cited by examiner

PRAZIQUANTEL FORMULATIONS

CROSS REFERENCE TO RELATED APPLICATIONS

This application is a continuation of U.S. patent application Ser. No. 16/991,397, filed Aug. 12, 2020, the entire contents of which are incorporated herein by reference.

TECHNICAL FIELD OF THE INVENTION

This invention is related to the area of formulations and treatments for parasite infections. In particular, it relates to praziquantel formulations.

BACKGROUND OF THE INVENTION

Praziquantel is a medication used to treat a number of types of parasitic worm infections. Specifically it is used for schistosomiasis, clonorchiasis, opisthorchiasis, tapeworm infections, cysticercosis, hydatid disease, and other fluke infections. Often the treatment with Praziquantel leads to unwanted side effects, such as gastrointestinal discomfort attributed to build up of immobilized or killed parasites. Reported side effects include: headache, dizziness, stomach pain, nausea, tiredness, weakness, joint/muscle pain, loss of appetite, vomiting, and sweating. These side effects can harm the patient and makes the experience of using the drug unpleasant and may discourage patient compliance with prescribed medicine.

Praziquantel ((RS)-2-(Cyclohexylcarbonyl)-1,2,3,6,7,11b-hexahydro-4H-pyrazino[2,1-a]isoquinolin-4-one) ($C_{19}H_{24}N_2O_2$) is represented as:

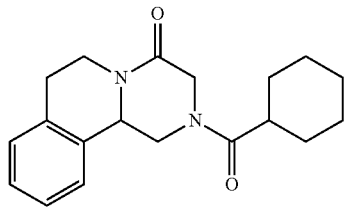 [SMILES: O=C(C1CCCCC1)N1CC(=O)N2CCc3ccccc3C2C1]

There is a continuing need in the art to treat parasites with reduced side effects.

SUMMARY OF THE INVENTION

According to one embodiment of the invention a liquid pharmaceutical formulation is provided. The formulation comprises: polyethylene glycol (PEG); rubusoside; and praziquantel.

Another embodiment is a method of treating an infection by a blood fluke or tapeworm in a patient. A liquid pharmaceutical formulation is administered to the patient. The formulation comprises: polyethylene glycol (PEG); rubusoside; and praziquantel.

Yet another embodiment is a powdered formulation of praziquantel for reconstitution in water and subsequent administration to a patient as a liquid formulation. The powdered formulation comprises: polyethylene glycol (PEG); rubusoside; and praziquantel.

In still another embodiment a powdered formulation of praziquantel is provided. The powdered formulation comprises: rubusoside; and praziquantel.

These and other embodiments which will be apparent to those of skill in the art upon reading the specification provide the art with improvements in patient compliance, satisfaction, comfort, and overall treatment experience.

DETAILED DESCRIPTION OF THE INVENTION

The inventor has developed a method of formulating praziquantel so that it is easily, accurately, and pleasantly administered and reduces one or more side effects associated with its use. Additional benefits to pharmacokinetic properties may also accrue.

The current practice in the art is to dispense praziquantel as a large tablet that must be split—sometimes into multiple segment—to achieve a proper dose for a patient. By using a powdered or liquid formulation, dispensing proper doses is easier, reducing errors, variations, and waste based on variations in pill splitting technique.

Praziquantel is only moderately soluble in water. According the Merck Index, its solubility is 400 mg/l. However, the combination of elements in the formulations as disclosed here are able to achieve a higher degree of solubility, permitting liquid dosing in a palatable volume. The liquid or powdered formulation comprises: polyethylene glycol (PEG); rubusoside; and praziquantel. The pharmacokinetic properties such as absorption may also be altered by this combination.

The ratio of rubusoside to praziquantel in the formulation may range from about 2:1 to about 10:1. This may be adjusted to achieve a suitable solubility level, gastrointestinal absorption, and agreeable taste profile.

In some cases the combination may be used to form a liquid formulation. In other instances it may be desirable to use it to form a tablet.

Polyethylene glycol as used in the liquid and powdered formulations has an average molecular weight large enough for the polymer to serve as an osmotic laxative. Typically this is between 2000 and 6000 daltons, between 3000 and 4500, or between 3200 and 3700. Popular commercially available versions are 3350, 4000 and 6000. The preparation of PEG may be polydisperse or monodisperse, for example. If polydisperse, then the molecular weight describes the weighted average molecular weight of the preparation. According to the formulations in powder or liquid form, the ratio of PEG to praziquantel may range between and including 5:1 and 10:1. In one embodiment the ratio is about 8:1.

For administration, the powdered form may be reconstituted in a liquid vehicle, either at the point of manufacture, at the dispensing pharmacy, or by the patient. The liquid vehicle may be water, a buffered aqueous solution, or an aqueous beverage, such as an energy drink or electrolyte rich drink. Alternatively, the powdered preparation of rubusoside and praziquantel may be constituted in a tablet or pill—with or without PEG. Suitable ingredients for a tablet or pill may include any or all of corn starch, magnesium stearate, microcrystalline cellulose, povidone, sodium lauryl sulfate, polyethylene glycol, titanium dioxide and hypromellose.

A variety of parasites and the diseases they cause may be treated using the formulations disclosed here. These include schistosomiasis (bilharzia, bilharziasis, or snail fever) caused by schistosomes, fluke infections caused by the trematode *Clonorchis sinensis* (Chinese or oriental liver fluke), trematodes *Opisthorchis viverrini* (Southeast Asian liver fluke) and *Opisthorchis felineus* (cat liver fluke), taeniasis or cysticercosis caused by the tapeworm species *Taenia saginata* (beef tapeworm), *Taenia solium* (pork tapeworm), and *Taenia asiatica* (Asian tapeworm), tiny tapeworms of the genus *Echinococcus* causing either cystic echinococcosis (hydatid disease) or alveolar echinococcosis.

Patients which are treated can be either human or veterinary. Commonly infected veterinary animals include horse, dog, cat, poultry, cattle, pigs, and ruminants. Any of these can be treated using the formulations disclosed here.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Compounding of Praziquantel with Rubusoside

Generally, ingredients are deposited into a sealed container with ethanol and vortex-mixed to form a solution. The solution is subjected to centrifugation. The ethanol is evaporated off and dried mixture is dissolved in water. This mixture is centrifuged again and the supernatant is filtered through a membrane. The flow-through is dried then forming the compounded praziquantel.

In a specific example of making the liquid praziquantel, it is mixed with Rubusoside to create a water soluble chemical. The formulation ratio (10/1) being 100 mg of Rubusoside to 10 mg praziquantel is prepared. Ingredients are deposited into a sealed container with 1 ml of ethanol and vortexed for 15 minutes to form a solution. Then the mixture is subjected to centrifugation at 12,000 rpm for 10 min. Next, the ethanol is evaporated off and the mixture is then dissolved in 1 ml of water. This mixture is centrifuged again at 12,000 rpm for 10 minutes and filtered through a 0.20 µm membrane and dried. The resulting mixture can be used to make a liquid formulation of praziquantel when reconstituted in water. This gives 110 mg solids in the formula at a 10/1 ratio.

To adjust sweetness and solubility this formula can vary from 2/1 ratio-10/1 ratio depending on conditions.

Example 2

Formulating the Compounded Praziquantel/Rubusoside in a Liquid

| | |
|---|---:|
| Praziquantel (liquid recipe 10/1) | 7,333.37 mg |
| Glycol 3350 | 5,666.67 mg |
| Croscarmellose sodium | 43.17 mg |
| Providone | 43.17 mg |
| Sodium Laurel Sulfate | 43.17 mg |
| Magnesium Stearate | 43.17 mg |
| Brilliant Blue FCF (Blue1) | 43.17 |
| Total | 13,216.22 mg |

Inactive ingredients and active ingredients (praziquantel liquid recipe 10/1 and Glycol 3350; see Example 1) are mixed to homogeneity. The mixture is then reconstituted with 2.667 oz of purified water and a flavor enhancer such as FLAVORx. The dose for an adult human is 20 mg of praziquantel per kg 3× daily, e.g., every 5 hours during wakeful hours.

The invention claimed is:
1. A liquid pharmaceutical formulation, comprising:
a. rubusoside; and
b. praziquantel, wherein the liquid formulation is prepared by steps comprising (i) dissolving rubusoside and praziquantel in ethanol to form a solution, (ii) evaporating the ethanol from the solution to form a dry mixture, and (iii) redissolving the dried mixture in water;
and wherein the rubusoside to praziquantel is in a molar ratio between 0.97:1 and 4.86:1.

2. The liquid pharmaceutical formulation of claim 1, wherein the liquid pharmaceutical formulation further comprises polyethylene glycol (PEG), and wherein the PEG is polydisperse and has an average molecular weight of 2000 to 6000.

3. The liquid pharmaceutical formulation of claim 1, wherein the molar ratio of rubusoside to praziquantel in the liquid pharmaceutical formulation is 4.86:1.

4. The liquid pharmaceutical formulation of claim 1, wherein the molar ratio of rubusoside to praziquantel in the liquid pharmaceutical formulation is about 0.97:1.

5. The liquid pharmaceutical formulation of claim 2, wherein (a) a weight ratio of PEG to praziquantel is between 5:1 and 10:1, and (b) the molar ratio of rubusoside to praziquantel is about 0.97:1.

6. A method of treating an infection caused by a blood fluke or tapeworm in a patient, the method comprising:
administering a liquid pharmaceutical formulation comprising rubusoside and praziquantel to the patient,
wherein the liquid pharmaceutical formulation is prepared by steps comprising (i) dissolving rubusoside and praziquantel in ethanol to form a solution, (ii) evaporating the ethanol from the solution to form a dry mixture, and (iii) redissolving the dried mixture in water, and wherein the rubusoside to praziquantel is in a molar ratio between 0.97:1 and 4.86:1.

7. The method of claim 6, wherein the molar ratio of rubusoside to praziquantel in the liquid pharmaceutical formulation is between 0.97:1 and 4.86:1.

8. The method of claim 7, wherein the molar ratio of rubusoside to praziquantel in the liquid pharmaceutical formulation is about 0.97:1.

9. The method of claim 6, wherein the patient is a human.

10. The method of claim 6, wherein the patient is a veterinary patient.

11. The method of claim 6, wherein the infection is schistosomiasis or Echinococcosis.

12. The method of claim 6, wherein the infection is caused by *Clonorchis sinensis, Opisthorchis viverrini, Opisthorchis felineus, Taenia Saginata, Taenia solium*, or *Taenia asiatica*.

13. The method of claim 10, wherein the veterinary patient is selected from the group consisting of a horse, a dog, a cat, poultry, and a ruminant.

14. The method of claim 6, wherein the liquid pharmaceutical formulation is administered to the patient at a dose of between 10 and 40 mg praziquantel per kg of patient weight.

15. The method of claim 6, wherein the patient is human and is administered the liquid pharmaceutical formulation 3 times daily, and wherein each administration of the liquid pharmaceutical formulation comprises between 10 and 40 mg praziquantel per kg of patient weight.

16. A powdered formulation of praziquantel suitable for reconstitution in water and subsequent administration to a patient as a liquid pharmaceutical formulation, said powdered formulation comprising rubusoside and praziquantel, wherein said powdered formulation is prepared by steps comprising (i) dissolving rubusoside and praziquantel in ethanol to form a solution, and (ii) evaporating the ethanol from the solution to form a dry mixture, wherein the dry mixture is suitable for reconstitution in water, and wherein the rubusoside to praziquantel is in a molar ratio between 0.97:1 and 4.86:1.

17. The powdered formulation of claim 16, wherein the powdered formulation further comprises polyethylene glycol (PEG) and wherein a weight ratio of the PEG to praziquantel is between 5:1 and 10:1.

18. The powdered formulation of claim 16, wherein the molar ratio of rubusoside to praziquantel in the powdered formulation is about 0.97:1.

19. A method of treating an infection caused by a blood fluke or tapeworm in a patient, the method comprising:
   administering the powdered formulation of claim 16 to the patient.

20. A method of treating an infection caused by a blood fluke or tapeworm in a patient, the method comprising:
   reconstituting the powdered formulation of claim 16 in water to form a liquid pharmaceutical formulation, and
   administering the liquid pharmaceutical formulation to the patient.

21. The powdered formulation of claim 16, wherein the powdered formulation is formed into a tablet or a pill.

22. The powdered formulation of claim 16, wherein the powdered formulation further comprises polyethylene glycol (PEG) having a molecular weight of 2000 to 6000.

\* \* \* \* \*